US00PP37229P2

(12) United States Plant Patent
Bourne

(10) Patent No.: US PP37,229 P2
(45) Date of Patent: Jan. 27, 2026

(54) GRAPEVINE NAMED 'SV34-134-463'

(50) Latin Name: *Vitis vinifera*
Varietal Denomination: SV34-134-463

(71) Applicant: Sunview Vineyards of California, Inc., Delano, CA (US)

(72) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 18/831,689

(22) Filed: Jul. 22, 2025

Related U.S. Application Data

(60) Provisional application No. 63/732,292, filed on Jul. 31, 2024.

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206
See application file for complete search history.

(56) References Cited

PUBLICATIONS https://www.fourwindsgrowers.com/products/autumn-seedless-grapevine?variant; 'Autumn Royal' grape; (Retrieved from the Internet on Nov. 13, 2025).*

* cited by examiner

*Primary Examiner* — Susan Mccormick Ewoldt
(74) *Attorney, Agent, or Firm* — Eric C. Cole; Baker Manock & Jensen, PC

(57) ABSTRACT

A new and distinct variety of grapevine plant named 'SV34-134-463' particularly characterized by its very large, dark black colored elliptical shaped berries that have a neutral flavor when grown under normal horticultural practices near McFarland, California.

3 Drawing Sheets

Latin name of the genus and species of the plant claimed: The plant claimed relates to a new and distinct variety of *Vitis vinifera.*

Variety denomination: The plant claimed shall be known as 'SV34-134-463'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV34-134-463'. As used herein, 'grapevine' refers to all plant parts including, vines, canes, tendrils, leaves, fruit and roots of 'SV34-134-463'. Grapevine named 'SV34-134-463' is the result of an effort to produce a late-ripening, black seedless table grape with fruit characteristics distinguishable from currently available cultivar 'Autumn Royal' (unpatented). This new cultivar originated from a cross conducted in May 2013 near McFarland, California between female parent grapevine selection 'SV17-50-583' (unpatented) and male parent grapevine cultivar 'SV19-28-68' (unpatented). Resultant ovules from the cross were harvested 42 days after pollination and cultured on 'Mccown's Woody Plant Medium'. Subsequently, the resultant embryonic plants were cultured in the same medium in the laboratory under twelve hours of light from fluorescent lights at 29° C. The seedlings from this effort were transplanted to the greenhouse in November of 2013 and grown in the greenhouse at 29° C. with 12 hours illumination under high pressure sodium vapor lamps. The seedling population of 187 plants was planted in the field in the spring of 2014 near Delano, California. The new grapevine was selected from this seedling population on Jul. 28, 2015. It was then propagated by cuttings and grafted to 'Freedom' (unpatented) rootstock near Delano, California in 2016. The present invention has been found to retain its distinctive characteristics through two successive asexual propagations.

Grapevine named 'SV34-134-463' differs from its female parent grapevine 'SV17-50-583' (unpatented) by having fruit with small, soft seed traces that are not noticeable when eating while the seed traces of grapevine 'SV17-50-583' (unpatented) are larger and partially lignified.

Grapevine named 'SV34-134-463' differs from its male parent grapevine 'SV19-28-68' (unpatented) by having berries that are elliptical in shape rather than the obovate berries of 'SV19-28-78' (unpatented).

Grapevine named 'SV34-134-463' most closely resembles commercially available grapevine 'Autumn Royal' (unpatented) from which it may be distinguished by its smaller, softer seed trace, whereas grapevine 'Autumn Royal' (unpatented) has a well-lignified seed trace.

SUMMARY OF THE INVENTION

The following are the most outstanding and distinguishing characteristics of the ripe fruit of this new variety when grown under normal horticultural practices near McFarland, California:

a. Very large, sweet berries with neutral flavor.
b. Crisp berry texture; and
c. Very dark, black berries which require no ethephon application.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from the original seedling vine and from grafted vines grown in a commercial trial.

DETAILED BOTANICAL DESCRIPTION

Figure 1:
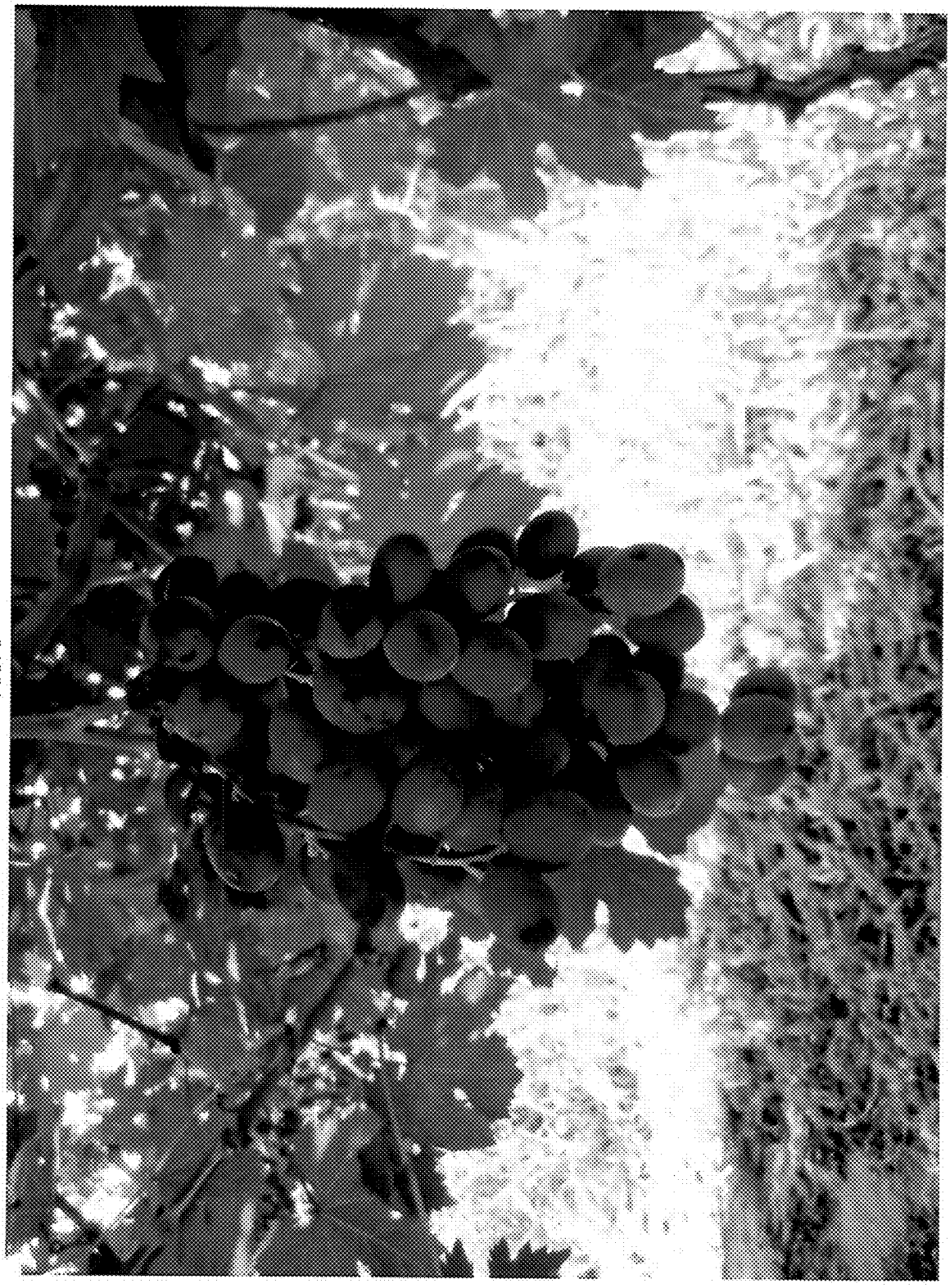
FIG. 1 Fruit cluster growing on seedling vine.
Figure 2:
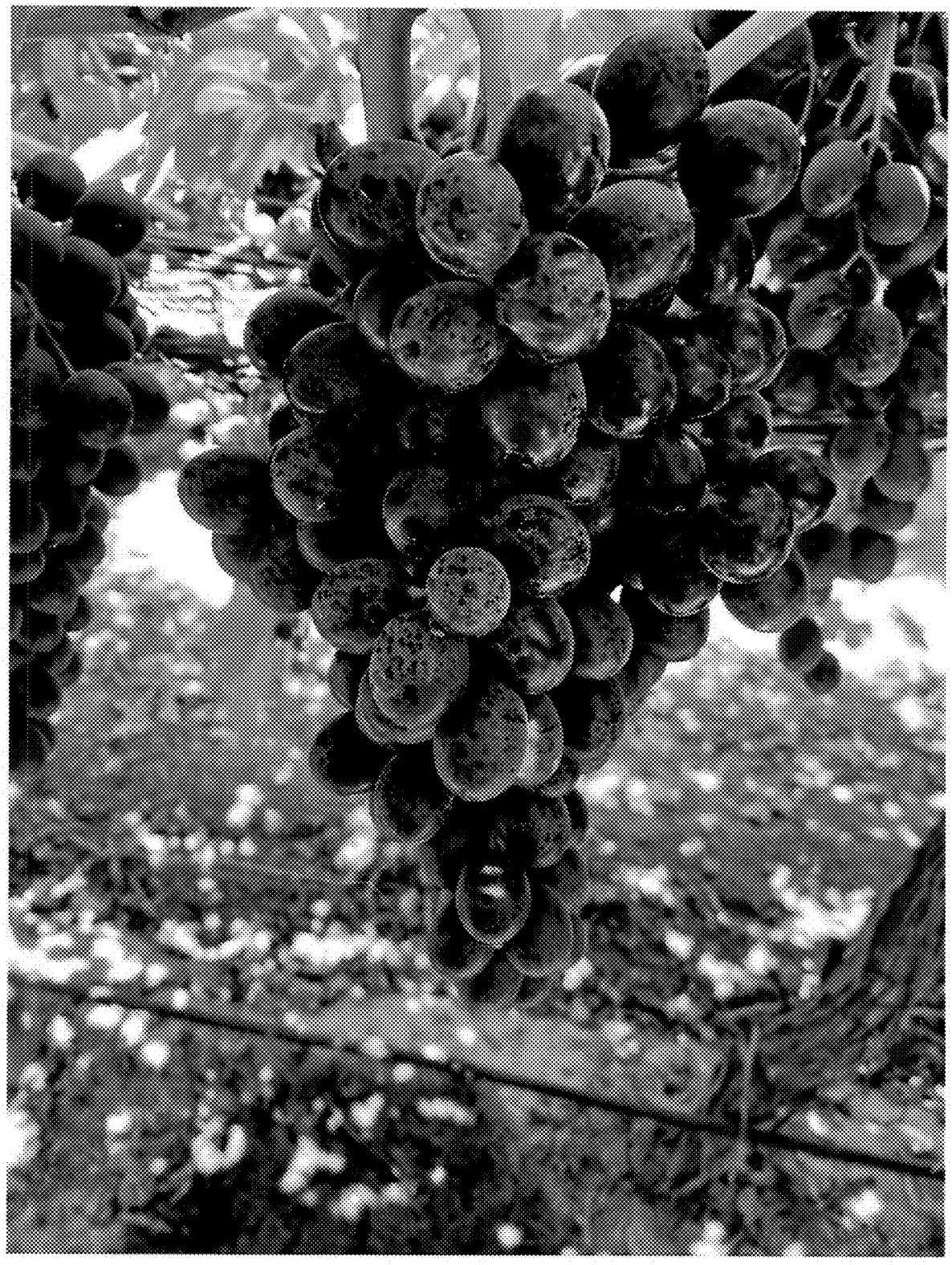
FIG. 2 Fruit cluster grown in commercial trial with no amendments or trunk girdling.
Figure 3:
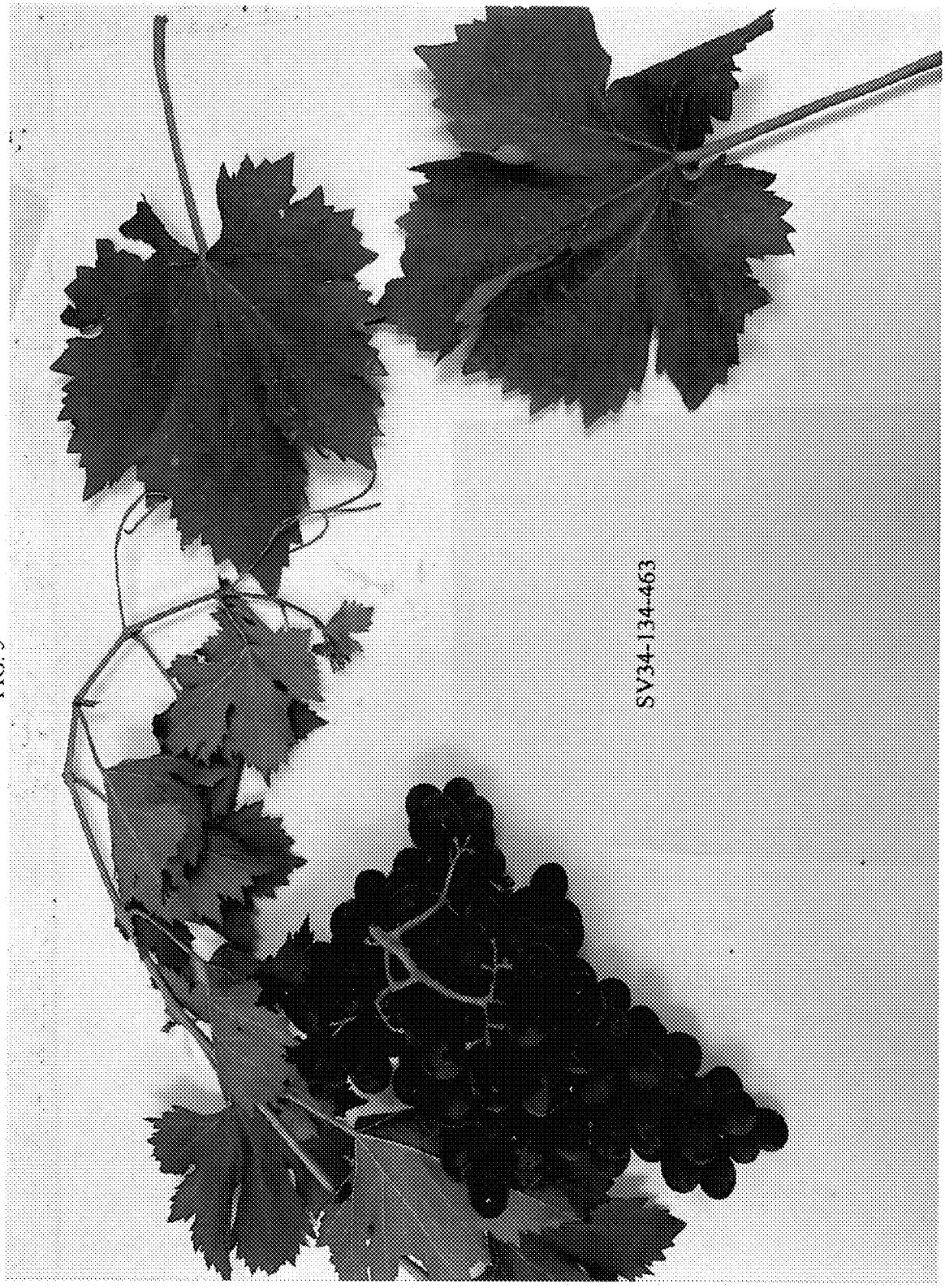
FIG. 3 Fruit, shoots, leaves and shoot apex from plant grown with no amendments or trunk girdling.

The following detailed description sets forth the distinctive characteristics of grapevine 'SV34-134-463'. Descriptions of the new invention apply to vines of grapevine 'SV34-134-463' grown on 'Freedom' (unpatented) rootstock at a density of 1,537 vines per hectare grown near Bakersfield, California in 2024. These vines were in their fifth year of production having been planted in 2018. These descriptions are believed to apply generally to the new variety grown under similar circumstances elsewhere. Variation due to soil and climatic conditions in other locations may be seen. References to color correspond to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:
- *Family*.—Vitaceae.
- *Botanical name*.—*Vitis vinifera*.
- *Variety name*.—SV34-134-463.

Plant:
- *Vigor*.—Vigorous; vines spur-pruned and shoot thinned to 32 shoots producing 261 cm of growth per cane.
- *Density of foliage*.—Dense.
- *Productivity*.—Very productive when spur pruned, up to 38,608 kg/hectare.
- *Hardiness*.—Hardiness observed to 0° C.
- *Rootstock*.—'Freedom' (unpatented).

Trunk:
- *Shape*.—Broadly elliptical.
- *Straps*.—Long, split.
- *Surface texture*.—Shaggy.
- *Trunk circumference*.—25.5 cm at 1.0 m of height.
- *Inner bark color*.—RHS Greyed orange group 174B.
- *Outer bark color*.—RHS Grey group 201A.

Mature leaves:
- *Average blade length*.—13.74 cm.
- *Average blade width*.—18.48 cm.
- *Size of blade*.—Medium.
- *Shape*.—Pentagonal.
- *Number of lobes*.—5.
- *Anthocyanin coloration of main veins on the upper side of the blade*.—Present at base of main veins (RHS Red-Purple group 60B).
- *Mature leaf profile*.—In plane of blade.
- *Blistering* (*upper surface*).—Absent.
- *Leaf blade tip*.—Curve downward.
- *Margins*.—Lobed, serrated, undulating.
- *Apex*.—Broadly acuminate.
- *Bases*.—Sagittate.
- *Thickness*.—Medium.
- *Undulation of blade between main and lateral veins*.—Slight.
- *Shape of teeth*.—Mix of both sides straight and both sides convex.
- *Length of tip*.—6 to 12 mm.
- *Width of tip*.—6 to 10 mm.
- *Ratio length/width of tip*.—About 1:1.
- *General shape of petiole sinus*.—Open.
- *Tooth at petiole sinus*.—Absent.
- *Petiole sinus limited by veins*.—Absent.
- *Shape of upper lateral sinus*.—Closed.
- *Depth of upper lateral sinus*.—Deep (avg. 4.4 cm).
- *Prostrate hairs between veins* (*lower surface*).—Absent.
- *Erect hairs between veins* (*lower surface*).—Absent.
- *Prostrate hairs on main veins* (*lower surface*).—Sparse.
- *Density of erect hairs on main veins* (*lower surface*).—Sparse only on junctions on main veins.
- *Prostrate hairs on main veins* (*upper surface*).—Sparse.
- *Upper surface*.—Summer color: RHS Green group 137A. Surface texture: Smooth. Surface appearance: Dull. Goffering of blade: Absent.
- *Lower surface*.—Summer color: RHS Green group 137C. Anthocyanin coloration of main veins on lower leaf surface: Present only at base of main veins. Anthocyanin coloration on laterals: Absent. Glossiness: Low. Pubescence distal portion of surface: Absent. Surface texture: Rough. Surface appearance: Dull.
- *Petiole*.—Length: 10.64 cm. Length of petiole compared to middle vein: Shorter. Density of prostrate hairs: Absent. Density of erect hairs: Absent. Shape of base of petiole sinus: Wide Open. Color: In shade: RHS Yellow-Green group 145B. In sun: RHS Red-Purple group 59A.

Tendrils:
- *Number & pattern*.—Trifurcated; forming irregularly above node 8.
- *Length*.—27.71 cm.
- *Diameter*.—4.2 mm.
- *Texture*.—Smooth.
- *Color*.—RHS Yellow-Green group 144A.

Growing tips (young shoot):
- *Prostrate hair on tips*.—Present.
- *Erect hairs on tips*.—Absent.
- *Color*.—RHS Yellow-Green group 144A.
- *Anthocyanins*.—Present.
- *Shape*.—Rounded.
- *Apex*.—Fully open.

Green summer shoots:
- *Shoot attitude*.—Erect.

*Internode color dorsal surface*.—RHS Yellow-Green group 144C.

*Internode color ventral surface*.—RHS Yellow-Green group 144C.

*Node color dorsal surface*.—RHS Yellow-Green group N144C and RHS Red-Purple group 59A.

*Node color ventral surface*.—RHS Yellow-Green group N144C.

Woody shoot:

*Canes*.—Shape: Broadly elliptical. Internode length: 9.62 cm. Width at node: 15 mm. Surface: Smooth. Main color: RHS Greyed-Orange Group 165B. Lenticels: Inconspicuous.

*Buds*.—Shape: Slightly pointed. Cane bud fruitfulness: Basal buds fruitful, usually 2 clusters per shoot. Length: 6.3 mm. Width: 4.5 mm. Height: 5 mm. Color: RHS Greyed-Orange Group 165A.

Flowers:

*Flower sex*.—Hermaphrodite.

*Position of first flowering nodes*.—4.

*Number of inflorescences per shoot*.—Usually 2.

*Flower cluster width*.—10.6 cm.

*Flower cluster length*.—22.2 cm.

*Cluster stem color*.—RHS Yellow green group 144A.

*Calyptra color*.—RHS Yellow green group 144A.

*Ovary length* (*mm*).—1.5 mm.

*Ovary width* (*mm*).—1 mm.

*Ovary color*.—RHS Yellow green group 143B.

*Filament length*.—2 mm.

*Filament color*.—RHS Yellow green group 145C.

*Anther length* (*mm*).—1 mm.

*Anther color*.—RHS Yellow 8B.

*Date of full bloom*.—May 14, 2024.

Fruit:

*Ripening period*.—Mid-season, Delano, California.

*Date of ripening*.—August 21, Delano, California.

*Use*.—Fresh market.

*Keeping quality*.—Very good.

*Shipping quality*.—Very good.

*Solids-sugar*.—19 brix.

*Total acidity*.—0.29.

*PH*.—3.84

*Bunch*.—Size: Large. Length (peduncle excluded): 22.7 cm. Width: 14.2 cm. Weight: Natural, without gibberellic acid treatment: 639 g. Density: slightly compact. Number of berries: 159. Form: conical

*Peduncle*.—Length: 3.5 cm. Lignification: none. Color: RHS yellow-green group 144A.

*Berry*.—Size: Medium. Uniformity of size: Uniform. Weight: Natural, without gibberellic acid treatment: 7.3 g. Shape: Natural, without gibberellic acid treatment: elliptic. Presence of seeds: Seedless; most berries develop one or two small, soft rudimentary seeds less than 1.0 mm in length. Cross section: Circular. Dimensions: Longitudinal axis: 2.2 cm. Horizontal axis: 1.8 cm. Skin color (without bloom): RHS Black Group 202A. Coloration of flesh: Translucent. Juiciness of flesh: Very juicy. Berry firmness: Meaty. Particular flavor: Neutral, typical *Vitis vinifera*. Bloom (cuticular wax): Strong. Pedicel length: 1.28 cm. Berry separation from pedicel: With difficulty; vascular traces well-developed.

*Skin*.—Thickness: Medium. Texture: Crisp. Reticulation: Absent. Roughness: Absent. Tenacity: Tenacious to flesh. Tendency to crack: Resistant.

Having thus described and illustrated my new variety of grapevine, I claim:

1. A new and distinct variety of grapevine plant named 'SV34-134-463', substantially as illustrated and described herein.

* * * * *